United States Patent [19]

Morgan et al.

[11] Patent Number: 4,610,254
[45] Date of Patent: Sep. 9, 1986

[54] INTERACTIVE PORTABLE DEFIBRILLATOR

[75] Inventors: Carlton B. Morgan; Daniel Yerkovich, both of Seattle; Thomas D. Lyster, Redmond; Douglas H. Roberts, Lynnwood, all of Wash.

[73] Assignee: Physio-Control Corporation, Redmond, Wash.

[21] Appl. No.: 587,439

[22] Filed: Mar. 8, 1984

[51] Int. Cl.$^4$ .............................................. A61N 1/36
[52] U.S. Cl. .................................................. 128/419 D
[58] Field of Search ..................... 128/419 D, 705; 364/415

[56] References Cited

U.S. PATENT DOCUMENTS

| | | | |
|---|---|---|---|
| 3,236,239 | 2/1966 | Berkovits | 128/419 D |
| 3,442,269 | 5/1969 | Druz | 128/419 D |
| 3,608,545 | 9/1971 | Novack et al. | 128/706 |
| 3,716,059 | 2/1973 | Welborn et al. | 128/419 D |
| 3,860,009 | 1/1975 | Bell et al. | 128/419 D |
| 4,096,856 | 6/1978 | Smith et al. | 128/419 D |
| 4,130,881 | 12/1978 | Haessler et al. | 364/415 |
| 4,165,749 | 8/1979 | Cansell | 128/419 D |
| 4,168,711 | 9/1979 | Cannon, III et al. | 128/419 D |
| 4,210,149 | 7/1980 | Heilman et al. | 128/419 D |
| 4,273,114 | 6/1981 | Barkalow et al. | 128/419 D |
| 4,290,114 | 9/1981 | Sinay | 364/415 |
| 4,296,755 | 10/1981 | Judell | 128/419 D |
| 4,303,075 | 12/1981 | Heilman et al. | 128/419 PG |
| 4,360,345 | 11/1982 | Hon | 434/262 |

FOREIGN PATENT DOCUMENTS 2000682 1/1979 United Kingdom ........... 128/419 D

OTHER PUBLICATIONS

Diack et al, "An Automatic Cardiac Resuscitator for Emergency Treatment of Cardiac Arrest", *Med. Instrumentation*, vol. 13, No. 2, Mar.-Apr. 1979, pp. 78-82.
Stratbucker et al, "Automatic Cardioversion Using Electronic Arrythmia Logic", *Rocky Mountain Eng. Society*, 1965, pp. 57-61.

*Primary Examiner*—William E. Kamm
*Assistant Examiner*—Mitchell J. Shein
*Attorney, Agent, or Firm*—Christensen, O'Connor, Johnson & Kindness

[57] ABSTRACT

A portable, interactive medical electronic device exemplified by a defibrillator. The device obtains information about a patient's condition, such as ECG and transthoracic impedance data, directly from the patient, and information pertinent to the treatment of the patient indirectly through an operator of the device, and produces a medically appropriate action such as a defibrillation shock in response. Indirect information is obtained through information processing means that includes means for prompting the operator of the device and means for receiving the operator's responses thereto. Prompts may include both questions and instructions, and in one embodiment the information processing means obtains the assent of the operator before causing the defibrillation shock. Indirect information may include information as to whether the patient is conscious, and as to whether or not cardiopulmonary resuscitiation has been performed. The ECG and transthroacic impedance data may be collected through a common pair of electrodes. In one embodiment the device produces an indication that the ECG data is invalid if the transthoracic impedance data indicates excessive motion on the part of the patient. When a difibrillation shock is determined to be medically appropriate, a control signal is produced that causes the charging of an energy storage means and the subsequent discharging of such energy storage means through the patient without further operator intervention. The device also includes a tape recorder for allowing later analysis of the use of the device, and means for holding the tape recorder drive means in a disengaged position until the device is opened for use. The device also includes testing means for enabling a person to test the condition of the device without opening the case in which it is enclosed, means for producing and recording a distinctive sound when and if a defibrillation pulse is delivered, and means for allowing the electrodes to be quickly disconnected so that emergency personnel can conveniently use the electrodes with their own equipment.

23 Claims, 20 Drawing Figures

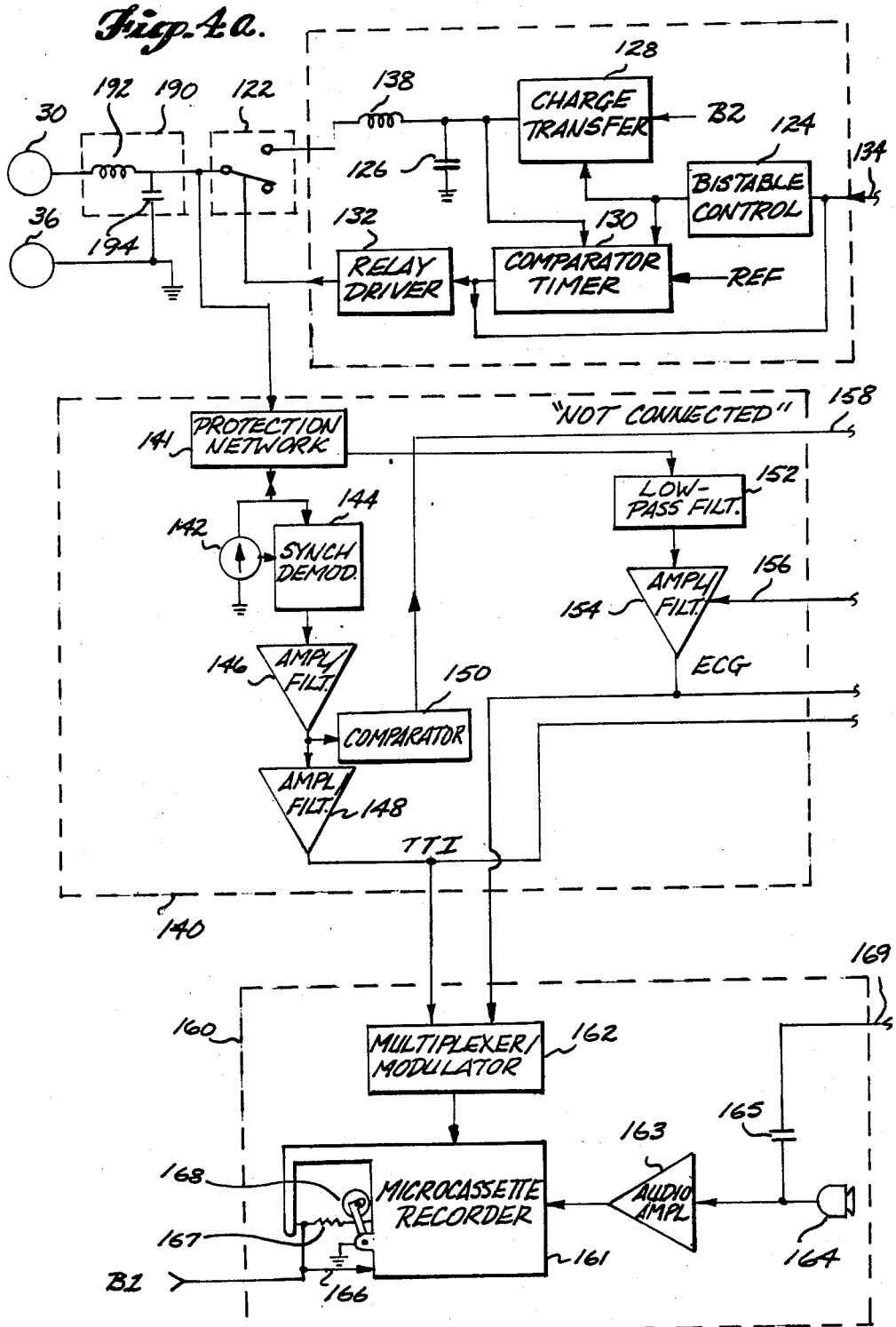

INTERACTIVE PORTABLE DEFIBRILLATOR

BACKGROUND OF THE INVENTION

It is well known that the probability of surviving a heart attack often depends critically on the speed with which appropriate medical care is provided. One of the most common and life threatening consequences of a heart attack is the development of a cardiac arrhythmia such as ventricular fibrillation in which the heart is unable to pump a significant volume of blood. When such an arrhythmia occurs, serious brain damage and death will invariably result unless a normal heart rhythm can be restored within a few minutes.

The most effective treatment for ventricular fibrillation is the application of a strong electric shock to the victim. By a mechanism not fully understood, such an electric shock frequently terminates the chaotic activity characteristic of arrhythmias, and restores the normal pumping action of the heart. Defibrillators for producing and delivering such shocks have been known and successfully used for many years. However, the size and cost of prior defibrillators, coupled with the risk they pose if used improperly, have restricted the use of defibrillators to hospitals and to emergency medical facilities. Many lives would be saved each year if defibrillators could be made more immediately available to heart attack victims.

A large number of heart attacks occur to people who have a history of cardiac problems, and who are therefore known to be at risk. In recent years, many family members of high risk patients have received training in cardiopulmonary resuscitation, a technique designed to maintain some blood flow even if the heart is in fibrillation or has stopped beating altogether. Such training is helpful because a large percentage of repeat heart attacks occur in the presence of a family member. Unfortunately, it has to date not been possible to provide the family members of high risk patients with access to the generally more effective technique of defibrillation, because of the difficulty of designing a defibrillator that is portable and that can be safely and effectively used by nonmedical personnel.

SUMMARY OF THE INVENTION

The present invention provides a personal defibrillator that is portable, easy to use, and comparatively inexpensive. The defibrillator is sufficiently compact and lightweight to be kept at all times in the immediate vicinity of a person known to be at risk to heart attacks. In addition, the defibrillator is designed to be used interactively, so that a properly trained, nonmedical operator can safely and effectively operate the device.

In one embodiment, the present invention comprises an interactive, medical electronic device that is capable of obtaining information about a patient's condition, such as ECG data, directly from the patient, and information pertinent to the treatment of the patient indirectly through an operator of the device, and for producing a medically appropriate action such as a defibrillation shock in response. Sensor means are used to obtain direct information concerning the condition of the patient, and indirect information is obtained through information processing means that includes means for prompting the operator of the device, and means for receiving the operator's responses thereto. The device also includes control means for producing a control signal when the direct and indirect information indicates that the medically appropriate action should be taken, and output means responsive to the control signal for producing such action. The information processing means may also include means for communicating questions and instructions to the operator, and means for obtaining the assent of the operator before producing the control signal. In one preferred embodiment, the questions communicated to the operator are designed such that appropriate responses are either YES or NO. The indirect information obtained from the operator preferably includes information as to whether the patient is conscious, and as to whether or not cardiopulmonary resuscitation has been performed.

In a further embodiment, the present invention comprises a defibrillator having means for simultaneously obtaining electrocardiogram and transthoracic impedance data from a patient, and means for producing an indication that the electrocardiogram data is invalid if the transthoracic impedance data indicates excessive motion on the part of the patient. In a preferred embodiment, the defibrillator includes means for producing analog electrocardiogram and motion signals, the motion signal being based on transthoracic impedance, and means for alternately sampling the electrocardiogram and motion signals and providing corresponding digital samples. A processor stores the electrocardiogram samples obtained during a time interval, and examines the motion samples provided during that time interval for indications of excessive motion on the part of the patient. If excessive motion is detected, the time interval is restarted. In a further preferred embodiment, electrocardiogram and transthoracic impedance data is collected through a common pair of electrodes.

In another embodiment of the present invention, a defibrillator is provided that includes information processing means for determining whether a defibrillation shock should be delivered and for providing a first control signal if the defibrillation shock should be delivered, and defibrillation means responsive to the first control signal for producing the shock. The defibrillation means includes energy storage means and means responsive to the first control signal for charging the energy storage means up to a threshold level and then discharging it through the patient. Timing means is provided for discharging the energy storage means through the patient if the charge on the energy storage means does not reach the threshold level within a predetermined time after the first control signal is provided. In a preferred embodiment, the defibrillation means provides a second control signal whenever the storage means is discharged, and the information processing means includes means for suspending its operations from the time that the first control signal is provided until the second signal is provided only upon command from an operator of the defibrillator, and the defibrillation means then proceeds to automatically charge and discharge the energy storage means.

In another embodiment, the present invention includes means for allowing medical personnel to analyze the circumstances in which the device was used. Such means comprises a tape recorder for recording signals representing medical information on magnetic tape, a source of electrical power, and switch means for connecting the source of electrical power to the tape recorder when the tape recorder is to be operated. The tape recorder includes drive means for driving the tape past a recording means, a portion of the drive means being movable between a first position in which the drive means engages and drives the tape, and a second position in which the tape is at least partially disengaged from the drive means. The movable portion of the drive means is biased towards the first position, and the tape recorder includes a conductive fusible link positioned to hold such portion in the second position. The fusible link is connected to pass an electrical current when the switch means connects the source of electrical power to the tape recorder, the fusible link being adapted to fuse when an electrical current is passed through it. The tape recorder is used to permanently record information concerning the use of the device. The fusible link prevents damage to the tape during long periods of storage before the device is used.

In another embodiment, the device of the present invention comprises a case, a battery enclosed within the case, and testing means enclosed within a case for enabling a person to test the condition of the device without opening the case. The testing means includes means for testing the device when battery power is applied and for producing an audible tone indicating the test results, and a magnetically operated switch adapted to connect the battery to the means for testing the condition of the device when a magnet is placed in the vicinity of the switch. The device of the present invention, including the battery, may therefore be placed within a completely sealed case, while still providing a means whereby the device or battery may be tested without opening the case or breaking the seal.

In another embodiment of the present invention, a defibrillator is provided having means for detecting that a defibrillation pulse has been delivered to the patient. The defibrillator includes a conductor through which the pulse is delivered, means responsive to the presence of current in the conductor for producing a magnetic field, means for producing a sound in response to the production of the magnetic field, and means for detecting the sound. The defibrillator may also include means for recording such sound on magnetic tape.

In another embodiment of the present invention, a defibrillator is provided having electrodes for attachment to a patient, defibrillation means for providing a pulse of electrical energy, and connector means for connecting the defibrillation means to the electrodes. The connector means includes plug means adapted to permit the electrodes to be quickly disconnected from the defibrillation means. When emergency medical personnel arrive on the scene, this feature enables them to avoid delay by plugging the electrodes of the present invention directly into their own equipment.

These and other features and advantages of the invention will become apparent in the detailed description and claims to follow, taken in conjunction with the accompanying drawings.

BRIEF DESCRIPTION OF THE DRAWINGS

FIG. 4a–b is a block diagram of the electronic components of the defibrillator.

DETAILED DESCRIPTION OF THE INVENTION

Figure 1:
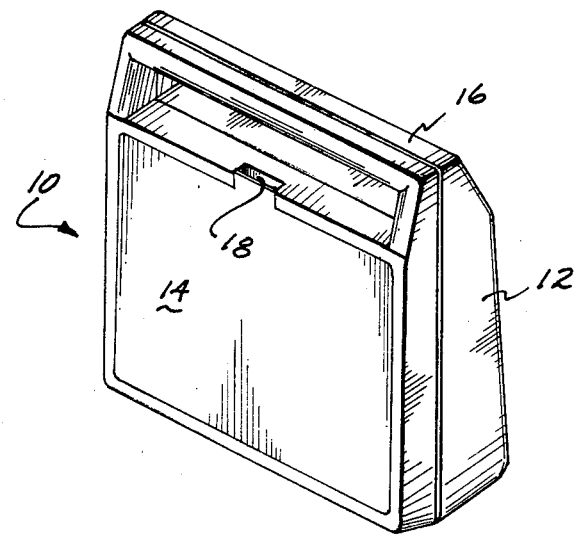
FIG. 1 is a perspective view of a sealed defibrillator according to the present invention.
Figure 2:
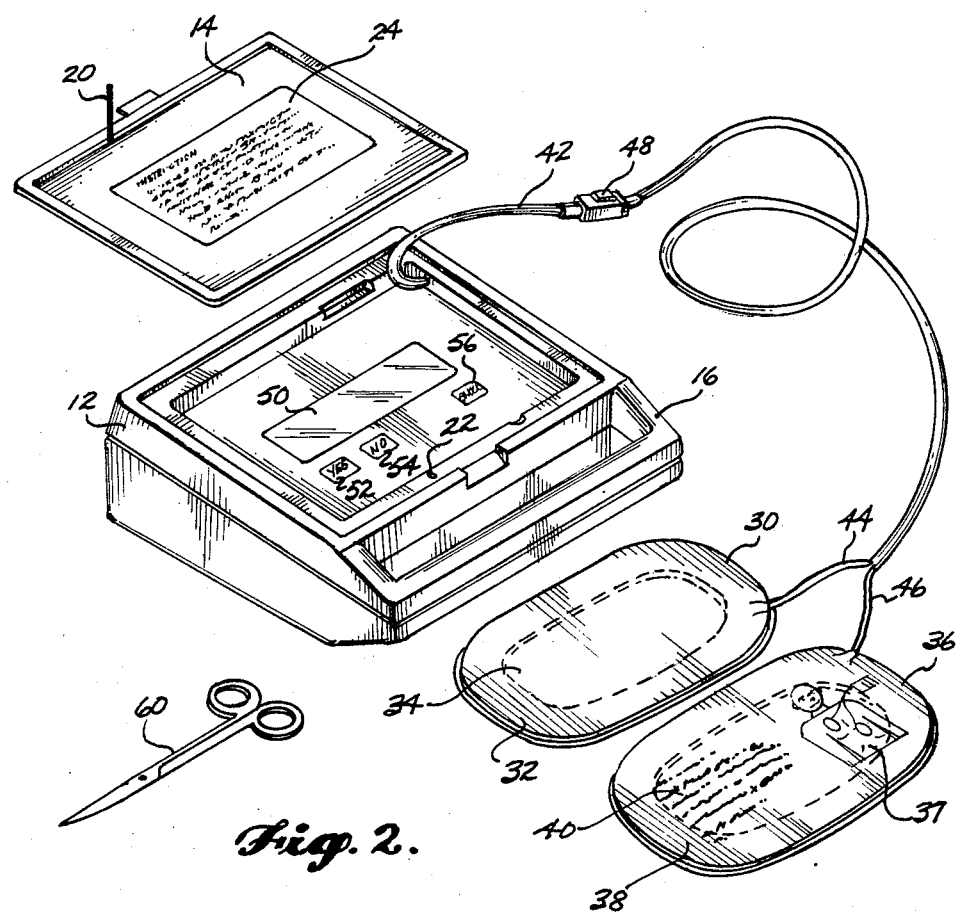
FIG. 2 is a perspective view of the defibrillator of FIG. 1 with the cover plate removed and the electrodes withdrawn.

Referring initially to FIGS. 1 and 2, one preferred embodiment of the present invention is shown as comprising defibrillator 10 having body 12, cover plate 14, and carrying handle 16. To use the defibrillator, an operator breaks seal 18 and removes cover plate 14. The cover plate includes a pin 20 which is positioned in opening 22 of body 12 before the cover plate is removed. Removal of the cover plate withdraws pin 20 and activates the defibrillator, as described below. The underside of cover plate 14 includes printed instructions 24 for facilitating correct usage of the device.

Prior to removal of the cover plate, a pair of electrodes 30, 36 and associated cable 42 are held in the space between cover plate 14 and body 12. When the cover plate is removed, the electrodes and cable may be withdrawn for use, as indicated in FIG. 2. Electrodes 30 and 36 include adhesively surfaced outer portions 32 and 38 respectively, and respective inner portions 34 and 40 that are coated with a conductive gel for making electrical contact with a patient's body. Cable 42 includes separate cables 44 and 46 connected to electrodes 30 and 36, respectively. Cable 42 includes plug 48 which permits the electrodes to be quickly disconnected from the defibrillator, so that emergency medical personnel arriving on the scene can avoid delay by plugging electrodes 30 and 36 directly into their own equipment. Electrode 36 includes diagram 37 illustrating the correct placement of the electrodes on the patient.

The body 12 of the defibrillator includes an LCD display 50, and pushbutton switches 52, 54 and 56. Display 50 is used for prompting the operator of the defibrillator, as described in greater detail below. Switches 52 and 54 are labeled with the words YES and NO, respectively, and are used by the operator to respond to questions presented via display 50. Switch 56 is labeled "SHOCK," and is used by the operator at the appropriate time to initiate application of a defibrillation shock.

A pair of scissors 60 may also be carried in the space between body 12 and cover plate 14. The scissors are used to remove the patient's clothing, to facilitate placement of electrodes 30 and 36.

Prior to use, the defibrillator of the present invention is completely contained within the portable, compact unit illustrated in FIG. 1. This design makes it both practical and convenient to continuously keep the defibrillator in the immediate vicinity of a patient known to be at risk with respect to heart attacks. Seal 18, in combination with other features described below, helps assure the integrity of the unit during prolonged periods of storage.

GENERAL OPERATION

Figure 3A:
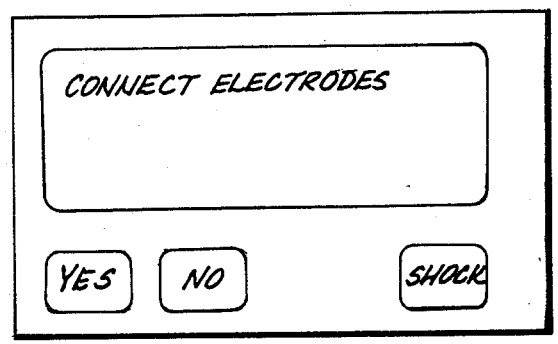
FIG. 3a–3h is a series of eight views of the display of the defibrillator during different stages of defibrillator operation.
Figure 3B:
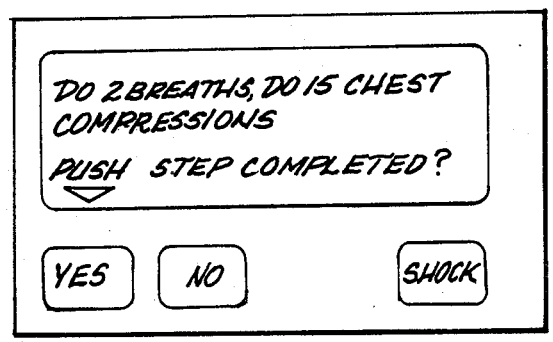
Figure 3C:
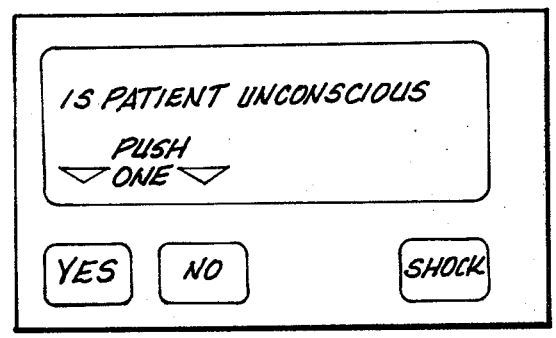

The general operation of the defibrillator will now be described with reference to FIGS. 3a–h. When a heart attack occurs, the operator removes the cover plate, and the defibrillator is activated electronically. The operator is immediately directed to connect the electrodes to the patient, as indicated in FIG. 3a. Diagram 37 (FIG. 1) on one of the electrodes is available to guide proper placement. When the instrument detects that the electrodes have been connected, the message indicated in FIG. 3b is displayed. This message directs the operator to perform standard CPR operations on the patient. The operator indicates that this step has been completed by pushing the YES switch. When the YES switch is pushed, or when 25 seconds has elapsed, the message shown in FIG. 3c is displayed. If the subject is not unconscious, then the operator pushes the NO switch, and the message shown in FIG. 3d will be displayed for a few seconds, after which the message in FIG. 3c will reappear. This feature allows the operator to respond appropriately if the patient later loses consciousness.

Figure 3D:
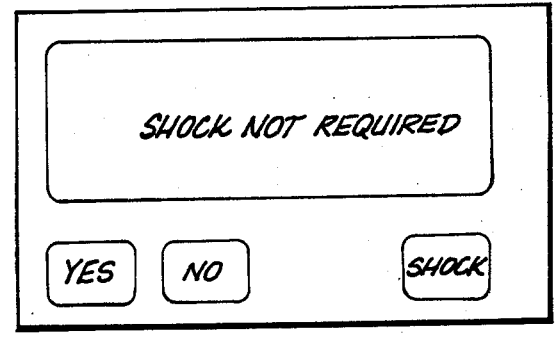
Figure 3E:
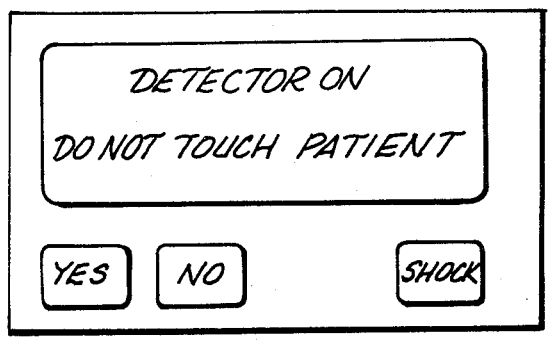
Figure 3F:
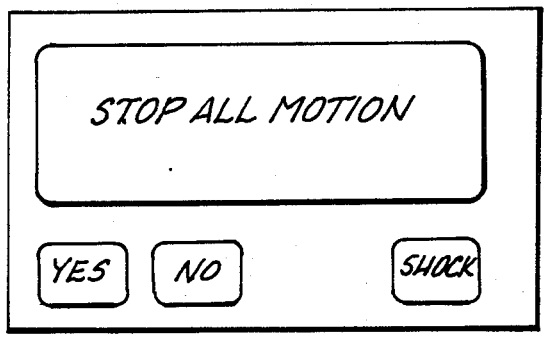

If the patient is unconscious, or becomes unconscious, then the operator pushes the YES switch (FIG. 3c), and the instrument enters a detection mode in which the message shown in FIG. 3e is displayed. In this mode, electrocardiogram (ECG) and transthoracic impedance data is obtained directly from the patient via electrodes 30 and 36 (FIG. 2). The resulting data is used, together with information supplied by the operator (e.g., subject unconscious), to determine whether a defibrillation shock is medically appropriate. During collection of data, the instrument looks for transthoracic impedance data that would indicate motion of the patient. If motion is detected, then the message shown in FIG. 3f is displayed, and the data collection is restarted.

Figure 3G:
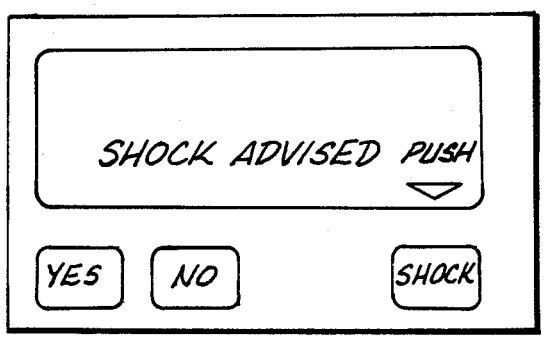
Figure 3H:
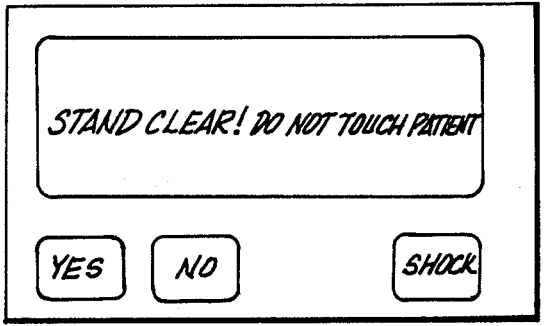

If the ECG data indicates that a defibrillation shock is not appropriate, then the message of FIG. 3d is briefly displayed, and the defibrillator then returns to the state corresponding to FIG. 3b. If the instrument determines that a shock is medically appropriate, then the message of FIG. 3g is displayed, advising the operator to proceed by pushing the SHOCK switch. If the SHOCK switch is then pushed, the instrument displays the message shown in FIG. 3h and then delivers a defibrillation shock to the patient. After the shock has been delivered, the instrument returns to the state corresponding to FIG. 3b. The cycle beginning at FIG. 3b and ending at FIG. 3h may be repeated for a maximum of two additional times, if the patient remains unconscious.

CIRCUIT DESCRIPTION

Figure 4B:
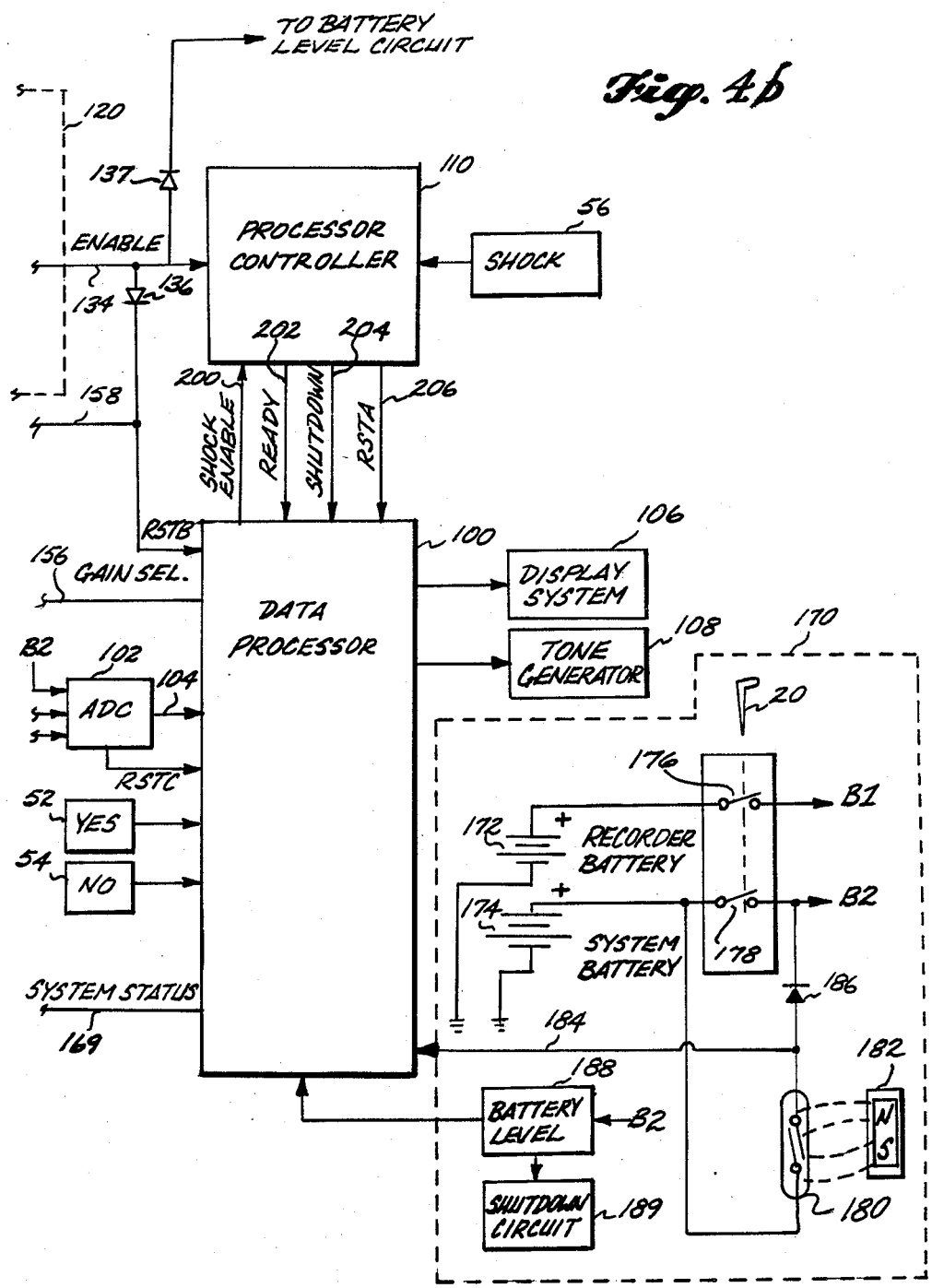

The body 12 of the defibrillator houses the electronic components illustrated in FIGS. 4a and 4b. These components include data processor 100, analog-to-digital converter (ADC) 102, processor controller 110, defibrillation circuit 120, analog preprocessor 140, data recorder 160, battery circuit 170, and various other components described below. Electrodes 30 and 36 are connected through electromagnetic interference filter 190 to defibrillation circuit 120 and to analog preprocessor 140. During the collection of ECG and transthoracic impedance data from the patient, relay 122 is in the position shown in FIG. 4a. The analog preprocessor separates the electrode signal into ECG and transthoracic impedance components, and delivers the component signals to ADC 102 and to data recorder 160. When a shock is to be delivered, the defibrillation circuit charges capacitor 126 up to a specified value, and then switches relay 122 such that capacitor 126 discharges through the patient via electrodes 30 and 36. After the shock has been delivered, relay 122 returns to the position shown in FIG. 4a.

BATTERY CIRCUIT

The electronic circuit of the present invention is activated when cover plate 14 is removed from the unit. Removal of the cover plate causes the withdrawal of pin 20, which in turn causes switches 176 and 178 (FIG. 4b) to close, connecting recorder battery 172 to microcassette recorder 161 and system battery 174 to the other components of the circuit in FIGS. 4a and 4b. The purpose of this feature is to prevent battery drain when the instrument is stored over extended periods of time. Means are provided, however, for permitting a person to check the condition of system battery 174 without opening or unsealing the instrument. This means comprises magnetic reed switch 180 connected in parallel with switch 178. The defibrillator of the present invention includes a separate battery test card having small magnets imbedded therein. To test the condition of system battery 174, a person holds the battery test card at a designated position adjacent to the outer surface of body 12. The magnet, indicated schematically by numeral 182 in FIG. 4b, closes reed switch 180 and provides power to all components of the defibrillator with the exception of microcassette recorder 161. The closing of reed switch 180 also supplies a test signal to data processor 100 on line 184. The test signal indicates to the data processor that a test is to be performed, and directs it to the appropriate procedure for carrying out the test. If the test is successful, the data processor causes tone generator 108 to emit a prescribed sequence of audible tones, to signal that the test has been successfully completed. Diode 186 prevents a test signal from being applied to data processor 100 during normal operation of the defibrillator, i.e., when switch 178 is closed.

During operation of the defibrillator, battery level circuit 188 continuously monitors the voltage available from system battery 174. If the voltage of system battery 174 falls below the level required for operation of data processor 100, then battery level circuit 188 activates shutdown circuit 189. Shutdown circuit 189 responds by cutting off power to data processor 100, thus preventing operation of the defibrillator at a voltage which might result in unreliable operation. A back-up system for preventing defibrillator operation when the battery level is too low is provided by ADC 102. ADC 102 periodically samples the system battery voltage (B2) and provides the digitized samples to data processor 100 over bus 104. As described below, the data processor will not advise or initiate a shock if such samples indicate insufficient battery voltage.

ANALOG PREPROCESSOR

The function of the analog preprocessor is to supply a constant current signal to the electrodes and to analyze the return signal. If the return signal indicates that the electrodes are not connected to the patient, then the analog preprocessor sends a NOT CONNECTED signal to the data processor. If the electrodes are connected, then the analog preprocessor extracts ECG signals and transthoracic impedance (TTI) signals from the return signal and sends the analog ECG and transthoracic impedance signals to data recorder 160 and analog-to-digital converter (ADC) 102.

The analog preprocessor includes protection network 141, constant current source 142, synchronous demodulator 144, amplifier/filters 146 and 148, comparator 150, low pass filter 152, and amplifier/filter 154. Associated with the analog preprocessor is electromagnetic interference filter 190 consisting of inductor 192 and capacitor 194. Constant current source 142 supplies a constant (RMS) current, 12 KHz sine wave which is applied to the patient through protection network 141 and electrodes 30 and 36. The resulting signal is synchronously demodulated by synchronous demodulator 144. The synchronous demodulator provides an output signal whose amplitude is proportional to the amplitude of the 12 KHz component of the return signal, i.e., to the impedance between electrodes 30 and 36. The output signal from synchronous demodulator 144 is passed to amplifier/filter 146. Amplifier/filter 146 removes unwanted high frequency components, including any residual 12 KHz signal, and also provides a small amount of gain. The output of amplifier/filter 146 is fed to amplifier/filter 148 and to comparator 150. Amplifier/filter 148 includes a bandpass filter with a passband of approximately 1–20 Hz. This filter thus removes the DC component from the return signal, and provides an output indicative of transthoracic impedance variations over time. Comparator 150 compares the level of the output of amplifier/filter 146 with a fixed reference voltage. If the level exceeds the reference, then the comparator pulls line 158 low, signaling that the electrodes are not connected.

The signal from electrodes 30 and 36 is also input to low pass filter 152 through protection network 141. The filter removes the 12 KHz signal and other high frequency components, and passes the resulting signal to amplifier/filter 154. Amplifier/filter 154 includes a bandpass filter adapted to extract the ECG signal returned from the patient through the electrodes. As further described below, amplifier/filter 154 also provides gain to the ECG signal, the amount of gain being determined by a digital GAIN SELECT signal originating in data processor 100 and transmitted to amplifier/filter 154 over line 156.

Protection network 141 is a conventional impedance matching network that protects the analog preprocessor from the high voltage applied to the electrodes by defibrillation circuit 120 during delivery of a shock to the patient. Protection network 141 has an impedance that does not signficantly affect ECG or transthoracic impedance measurements, but that does cause the attenuation of the frequency components contained in a defibrillation pulse to a degree sufficient to prevent such a pulse from damaging any of the components of the analog preprocessor.

DATA PROCESSOR

Data processor 100 is a conventional digital computer that includes a microprocessor, read only memory (ROM) for storing a program, random access memory (RAM) for data storage, a parallel port and a timer. A suitable microprocessor for use in data processor 100 is the NSC 800 microprocessor available from the National Semiconductor Corporation.

Associated with data processor 100 are processor controller 110 and associated SHOCK pushbutton switch 56, display system 106, tone generator 108, YES and NO pushbutton switches 52 and 54, and ADC 102. Processor controller 110 coordinates the activities of data processor 100 and defibrillation circuit 120, and is described in greater detail below. Display system 106 comprises a conventional display driver and LCD display unit 50 (FIG. 2). Tone generator 108 is a conventional audio transducer used for producing audible signals. Pushbutton switches 52, 54 and 56 correspond to the pushbuttons shown in FIGS. 2 and 3, and are used by the operator to respond to prompts communicated through display system 106, and to initiate a defibrillation shock. ADC 102 is an analog-to-digital converter used for converting the analog TTI and ECG signals from analog preprocessor 140 into digital signals usable by data processor 100. ADC 102 alternately samples the TTI and ECG signals at 240 Hz, thus providing a sampling rate of 120 Hz for each signal. The digital samples are passed to the data processor over 8-bit bus 104. ADC 102 provides an interrupt signal RSTC to data processor 100 each time a digital sample is ready. In response to the RSTC interrupt, data processor 100 jumps to an interrupt service routine for inputting the sample. Through this arrangement, a uniform sampling rate is provided regardless of the timing of the program for operating data processor 100.

DEFIBRILLATION CIRCUIT

Defibrillation circuit 120 is activated by a high ENABLE signal on line 134. In response to such a signal, the defibrillation circuit begins charging capacitor 126 from system battery 174 (B2). When the charge reaches a predetermined threshold, the defibrillation circuit energizes relay 122, discharging capacitor 126 through the patient through electrodes 30 and 36.

The defibrillation circuit is activated by a high ENABLE signal momentarily appearing on line 134. In response to this signal, bistable control circuit 124 latches line 134 into a high state, and causes charge transfer circuit 128 to begin charging capacitor 126 from system battery supply B2. Bistable control circuit 124 may, by way of example, consist of two amplifiers connected in series, with positive feedback means provided to enable the circuit to be stable in either one of two states. Charge transfer circuit 128 may be any well known circuit for converting a low level DC voltage to a high voltage output by means of a flyback transformer or other conventional means.

As capacitor 126 is charged through charge transfer circuit 128, the voltage on capacitor 126 is continuously monitored by comparator/timer 130. When the capacitor voltage exceeds a threshold level, comparator/timer 130 triggers relay driver 132 which in turn energizes the coil of relay 122, switching the relay and connecting capacitor 126 to the electrodes. The capacitor then discharges through the patient via wave shaping inductor 138. At the same time that comparator/timer 130 triggers relay driver 132, it also pulls line 134 low Bistable control circuit 124 then latches line 134 into a low state, completing the defibrillation cycle. Should capacitor 126 fail to charge to the threshold level within a predetermined time interval, then a timeout circuit included within comparator/timer 130 triggers relay driver 132 and pulls line 134 low, thus delivering to the patient whatever energy is available and terminating the defibrillation cycle.

As previously described, analog preprocessor 140 pulls line 158 low when it detects that electrodes 30 and 36 are not connected to the patient. One effect of line 158 going low is that line 134 is also pulled low through diode 136. A low voltage on line 134 will cause bistable control circuit 124 to latch line 134 in its low state, terminating any defibrillation cycle that is in process. Thus the defibrillator of the present invention will not attempt to deliver a defibrillation pulse should the electrodes become disconnected. Line 134 is also connected to battery level circuit 188 through diode 137. Thus when battery level circuit 188 detects a low voltage on system battery B2, line 134 will be held low, and the delivery of a defibrillation shock will also be prevented in this circumstance.

PROCESSOR CONTROLLER

Processor controller 110 coordinates the activities of data processor 100 and defibrillation circuit 120. When the data processor determines that a shock is advised (see FIG. 3g), it sends a high SHOCK ENABLE signal to processor controller 110 on line 200. This signal activates SHOCK pushbutton switch 56, such that if switch 56 is now pushed, a high ENABLE signal will be sent to defibrillation circuit 120 on line 134, initiating a defibrillation cycle. At the same time that line 134 is driven high, processor controller 110 sends a low READY signal back to data processor 100 on line 202. A short time after the READY signal is sent, processor controller sends a low SHUT DOWN signal on line 204. The SHUT DOWN signal causes data processor 100 to go into a quiescent state in which only its timer continues to be active. The READY signal is used by data processor 100 to prepare for entering this quiescent state. The purpose of this feature is to prevent any electromagnetic interference that might accompany the delivery of a shock to interfere with the operations of the data processor. After a shock has been delivered, processor controller 110 pulls lines 202 and 204 high to restart the data processor, and then issues a high RSTA interrupt signal on line 206, causing the data processor to go back to the state corresponding to the display in FIG. 3b, starting another cycle.

Figure 5:
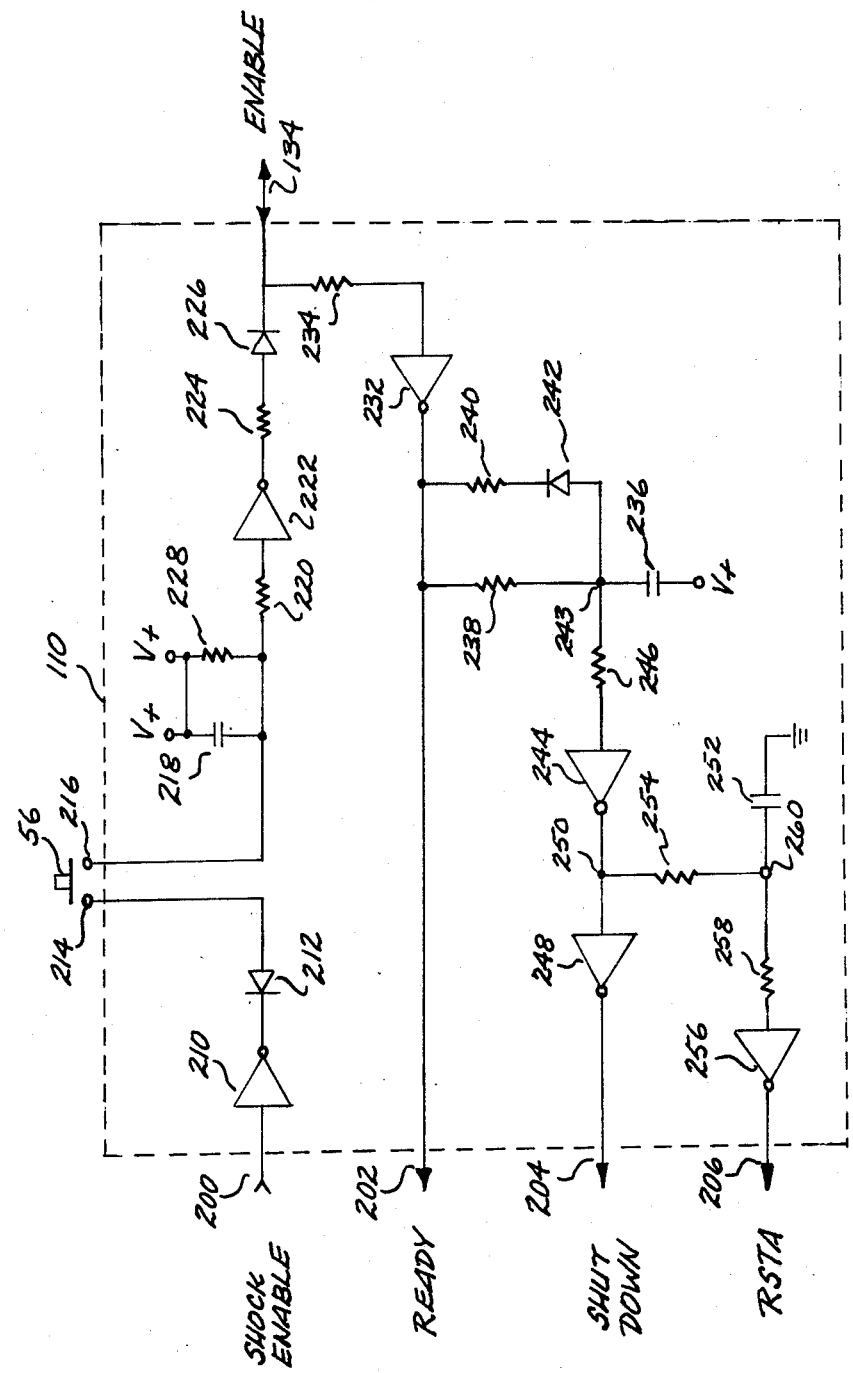
FIG. 5 is a circuit diagram of the processor controller.
Figure 7F:
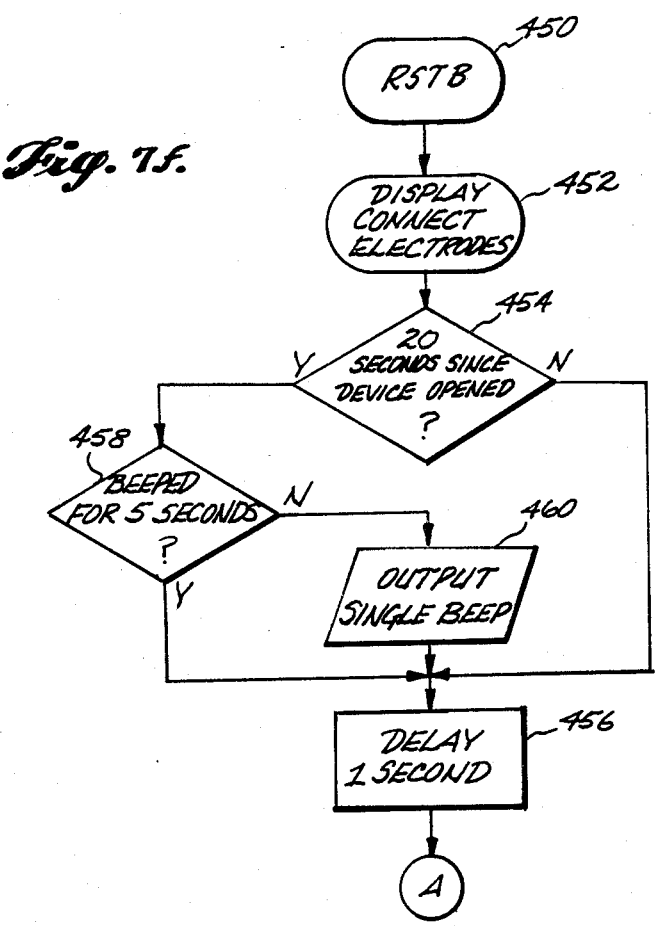
FIG. 7a–f is a flow chart of a program for operation of the data processor of the defibrillator.

The detailed construction of processor controller 110 is illustrated in FIG. 5. A high SHOCK ENABLE signal appearing on line 200 causes inverter 210 to supply a low voltage to terminal 214 of shock switch 56. When shock switch 56 is closed, terminal 216 is also driven low, enabling capacitor 218 to rapidly charge through switch 56. The resulting low voltage is input to inverter 222 through input resistor 220, driving line 134 high through resistor 224 and diode 226. When switch 56 is released, capacitor 218 discharges through resistor 228 at a rate slow enough to enable bistable control circuit 124 (FIG. 4a) to latch line 134 into a high state. After capacitor 218 discharges, diode 226 provides isolation between line 134 and inverter 222. Diode 212 prevents capacitor 218 from discharging through switch 56.

The high voltage on line 134 is sensed by inverter 232 through input resistance 234, causing inverter 232 to drive line 202 low. A low signal on line 202 causes data processor 100 to execute various housekeeping steps in preparation for line 204 going low. A low signal on line 202 also causes capacitor 236 to begin charging through resistor 238 and through resistor 240 and diode 242. The decreasing voltage at node 243 is coupled to inverter 244 through input resistor 246. When the voltage at node 243 has dropped below a certain level, a low signal appears on line 204, halting the operations of data processor 100. The delay between the SHUT DOWN and READY signals is determined by the time constant for the charge of capacitor 236.

At the time that line 204 is pulled low, node 250 goes high, and capacitor 252 begins to charge through resistor 254. The rising voltage at node 260 is coupled to inverter 256 through input resistor 258. When the voltage of node 260 has risen to a sufficient level, inverter 256 causes a low RSTA signal to appear on line 206. Since data processor 100 is shut down, the low RSTA signal has no effect at this time.

When a defibrillation cycle is completed, or when a low battery or a NOT CONNECTED signal is provided by analog preprocessor 140, line 134 is pulled low. Such a low signal initiates a sequence of events which is the reverse of that just described. In particular, a low signal on line 134 immediately drives line 202 high, and drives line 204 high a short time later, restarting the data processor. After another short time interval, processor controller 110 sends a high RSTA interrupt signal on line 206, vectoring data processor 100 to an appropriate restart point as described below.

DATA RECORDER

Data recorder 160 comprises microcassette recorder 161, multiplexer/modulator 162, audio amplifier 163, microphone 164, and coupling capacitor 165. Microcassette recorder 161 is powered by separate recorder battery (B1) 172, which is connected to the microcassette recorder through a normal conductor line 166 and through fusible link 167. Fusible link 167 consists of a piece of thin wire that melts as soon as current begins to flow through it, i.e., when cover plate 14 is removed and switch 176 closes. Prior to melting, fusible link 167 holds spring loaded pinch roller 168 out of engagement with the tape and capstan of microcassette recorder 161. This feature is provided so that the defibrillator of the present invention will be usable after an extended period of storage. During use, pinch roller 168 provides the pressure between the tape and capstan to enable the capstan to drive the tape. Prior to use, however, the fusible link holds the pinch roller disengaged from the capstan and tape to prevent it from flattening and sticking to the tape.

Microcassette recorder 161 is a two track recorder, one track for transthoracic impedance and ECG data, and the second track for voice and status information. Multiplexer/modulator 162 receives the analog transthoracic impedance and ECG signals from analog preprocessor 140, converts these analog signals to pulse-width modulation format, and multiplexes the resulting pulse streams for recording on one track of microcassette recorder 161. The other track of the microcassette recorder records voice and other audio signals picked up by microphone 164 and amplifier by audio amplifier 163. The voice track also records system status information sent by data processor 100 through line 169. The status information is coupled from line 169 to audio amplifier 163 through coupling capacitor 165.

Figure 6:
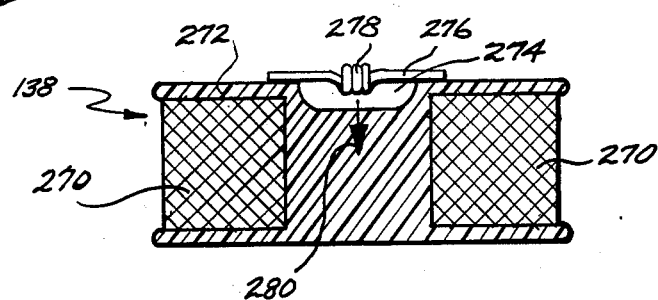
FIG. 6 is a cross-sectional view of the wave shaping inductor and associated sound producing means of the defibrillator.

The defibrillator of the present invention includes means by which data recorder 160 can record information confirming that a substantial amount of energy, i.e., a defibrillation pulse, has actually been delivered to the patient through electrodes 30 and 36. Referring to FIG. 6, a cross section of wave shaping inductor 138 is shown including bobbin 272 and inductor coils 270. The central portion of bobbin 272 is indented to form recess 274. Elastic cord 276 is mounted to bobbin 272 over recess 274, and mounts ferrous objects 278 thereon such that the ferrous objects are normally held over the recess spaced apart from the bobbin.

When a defibrillation pulse is delivered through wave shaping inductor 138, the current through inductor coils 270 creates a maximum magnetic field density in the direction indicated by arrow 280 that pulls ferrous objects 278 with considerable force into bobbin 272 at the base of recess 274. The unique sound caused by the objects striking the bobbin is picked up by microphone 164 and recorded on the voice track of microcassette recorder 161. These sounds can later be identified to confirm that defibrillation pulses have actually been delivered. After a defibrillation pulse, ferrous objects 278 return to the position indicated in FIG. 6, ready for a subsequent pulse to be recorded.

DATA PROCESSOR OPERATION

FIGS. 7a through 7f illustrate a flow chart for a program suitable for operation of the microprocessor of data processor 100. Block 300 represents the point at which program execution begins when power is first supplied to the microprocessor, or when line 204 (FIG. 4b) goes high. Block 302 tests the status of line 184 (FIG. 4b) to determine whether the power-on is a result of a test or actual operation of the device. If it is a test, then control passes to block 304 where appropriate tests are performed to verify that system battery 174 has sufficient voltage and that data processor 100 is capable of proper operation. In one embodiment, block 304 tests a digitized battery voltage sample provided by ADC 102 over bus 104. Block 306 determines whether the tests have been successfully passed. If they have not, then control returns to block 304 and the tests are repeated. If the tests are passed, then block 308 causes tone generator 108 to beep three times, block 310 delays program execution for three seconds, and control then returns to block 304 to repeat the tests. In the usual case, the person performing the test procedure will remove the magnet (test card) 182 when the beeps are generated, terminating the test and shutting down the system. If the three beeps are not heard, it is an indication that the tests have not been passed and that maintenance is required.

When the power-on (in block 300) is due to an actual opening of the defibrillator, then control passes from block 302 to block 312 where variable CPR is set to 1. This variable controls the number of times that the CPR sequence (FIG. 3b) is repeated, as described below. Block 316 then enables interrupts RSTA and RSTB. Interrupt RSTA is used to restart the microprocessor after a defibrillation shock has been delivered. The RSTA restart point is indicated by entry point 314, so that program execution returns at block 316 after a shock has been delivered. Referring to FIGS. 4a and 4b, interrupt RSTB is provided whenever a NOT CONNECTED signal is generated by analog preprocessor 140. In response to an RSTB interrupt, the microprocessor executes the interrupt service routine shown in FIG. 7f, and then returns control to the main program at entry point A, recommencing execution with block 312.

When the defibrillator is first opened for actual operation, electrodes 30 and 36 will not be connected, and the analog preprocessor will pull line 158 low, causing an RSTB interrupt signal to be sent to data processor 100. In this circumstance, the enabling of interrupt RSTB in block 316 will cause an immediate jump to block 452 of the interrupt service routine of FIG. 7f. Block 452 generates the display shown in FIG. 3a, and block 454 checks to see whether 20 seconds have elapsed since the defibrillator was opened. If 20 seconds have not elapsed, program execution is delayed for one second by block 456, after which program flow returns to block 312 in FIG. 7a. If the electrodes are not yet connected, interrupt RSTB will immediately vector the program back to the interrupt service routine, and this loop will continue until the electrodes are connected and interrupt RSTB is no longer present. For the first 20 seconds after the device is opened, block 454 causes a jump directly to block 456 each time the interrupt service routine is executed. Between 20-25 seconds after the device is opened, blocks 454 and 458 direct control through block 460 and a series of beeps is produced. After 25 seconds the beeps terminate and the program loops between the interrupt service routine and the main routine until the electrodes are connected.

Figure 7A:
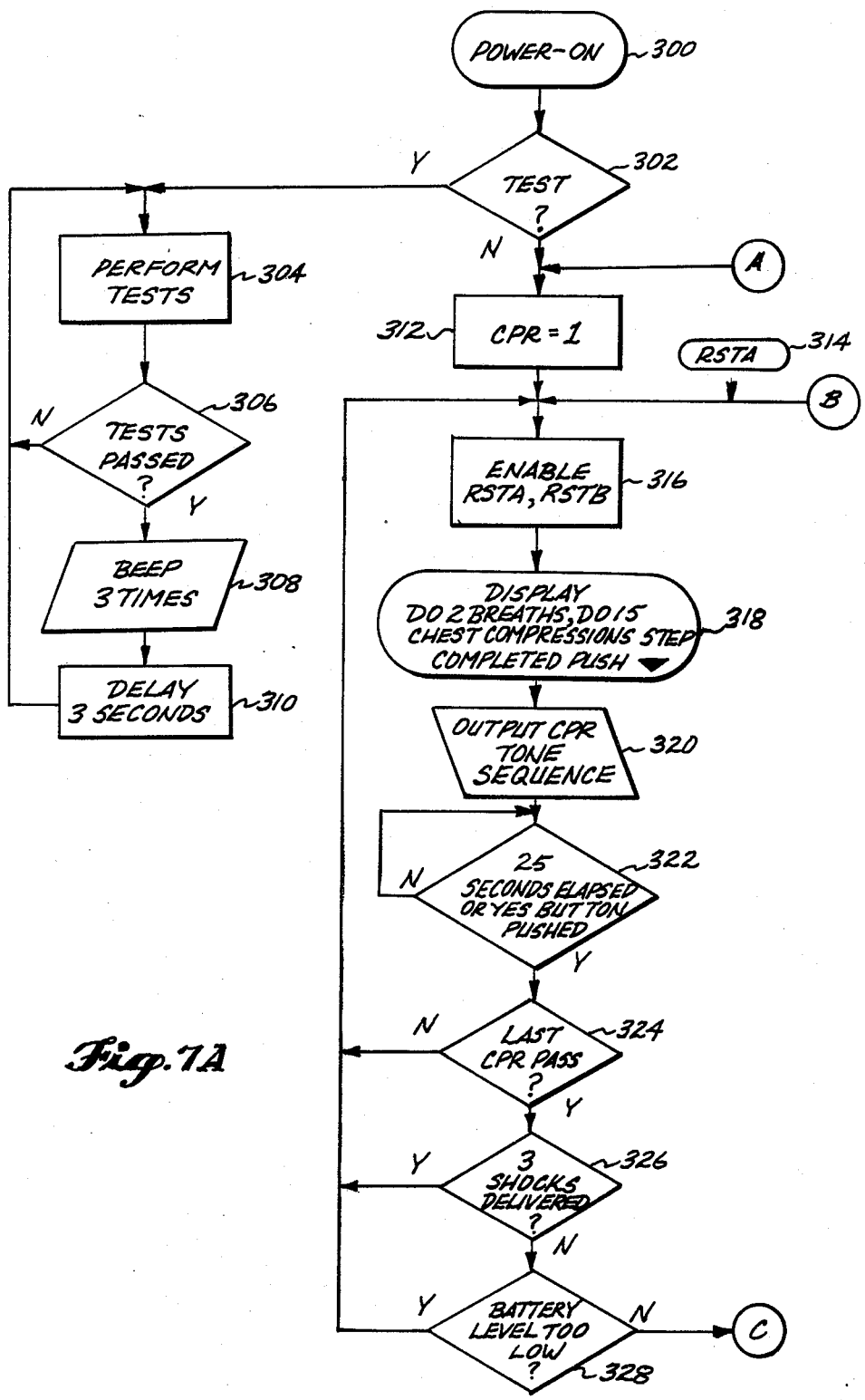
Figure 7B:
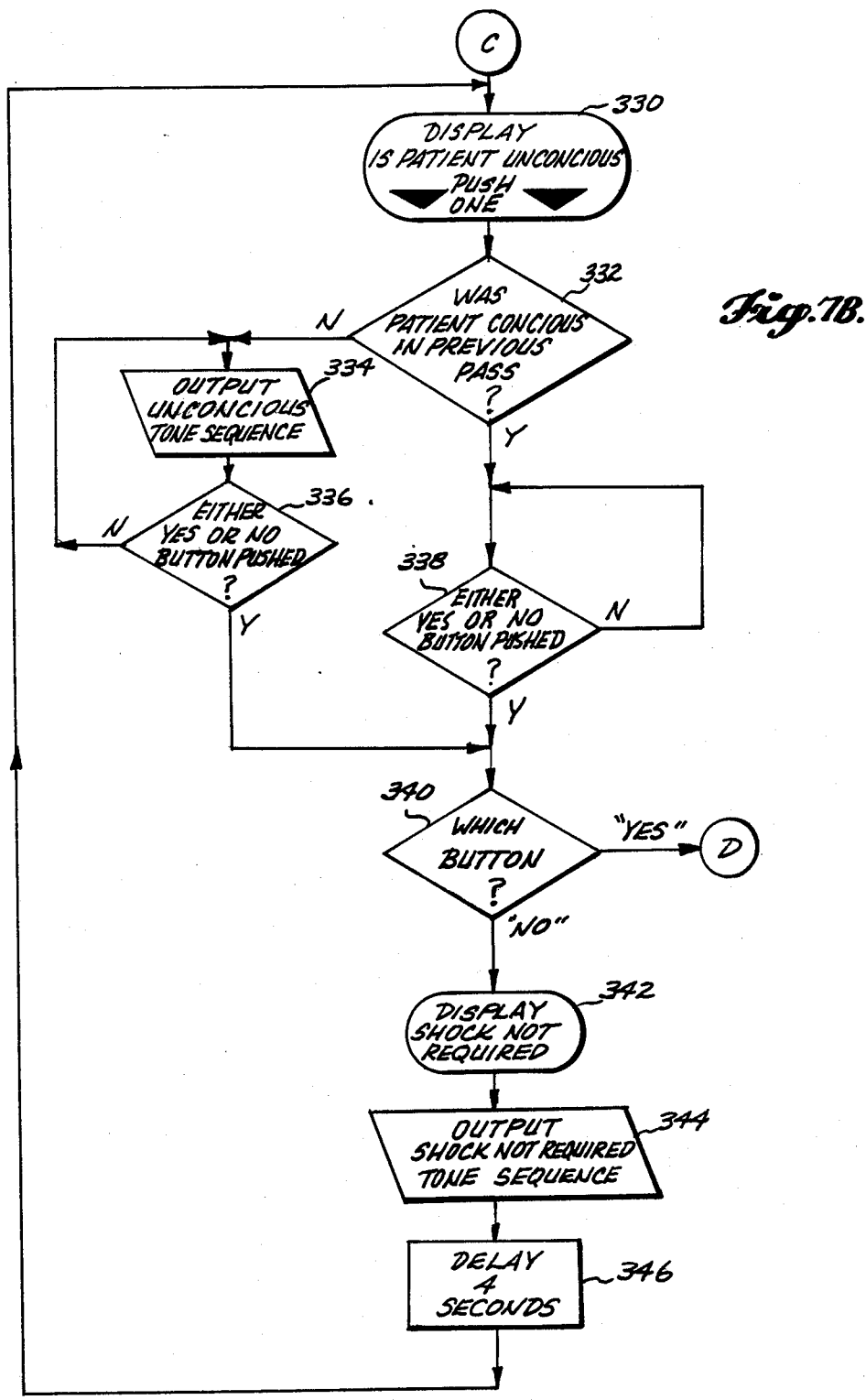
Figure 7C:
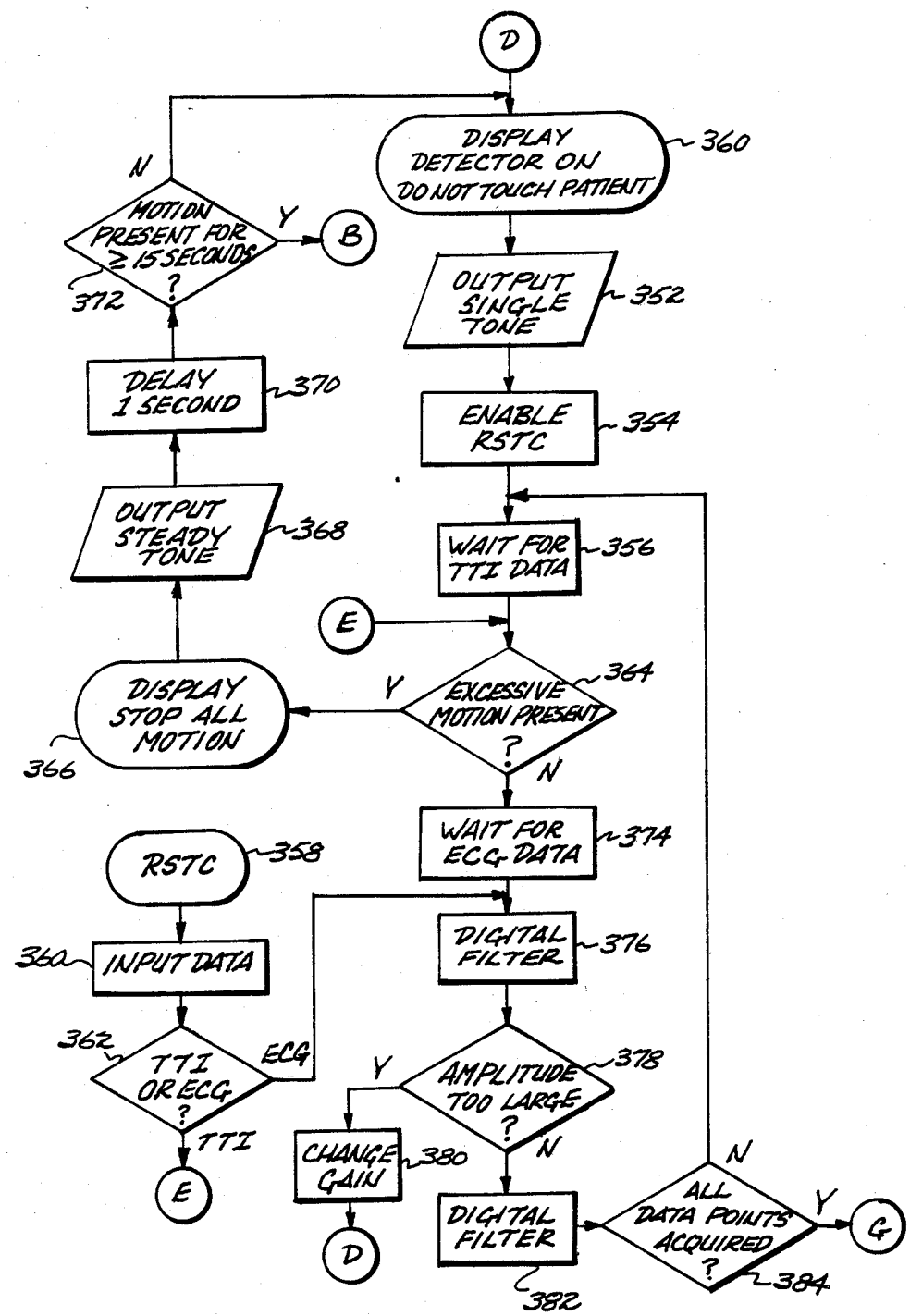

When the electrodes are connected, interrupt RSTB is no longer present and control passes through block 316 to block 318, where the message indicated in FIG. 3b is displayed. Block 320 then causes generation of a characteristic tone sequence, and block 322 tests to see whether YES pushbutton switch 52 has been pressed. When the YES switch is pushed, or when 25 seconds have elapsed, control passes to block 324 where the number of passes through the loop consisting of blocks 316-322 is compared to variable CPR. After a poweron, this test will be satisfied after the first pass, since CPR was set to 1 in block 312. Whenever this test is not satisfied, program execution returns to block 316, and another CPR sequence is performed. When the number of CPR sequences specified by variable CPR have been completed, control passes to block 326 which checks the number of shocks that have been delivered. The defibrillator of the present invention is intended to deliver up to a maximum of three defibrillation shocks. If three shocks have already been delivered, then block 326 returns control to block 316, and the CPR sequence is continued indefinately. If three shocks have not been delivered, then control passes to block 328, where the voltage level of system battery 174 is checked by examining the battery voltage sample provided by ADC 102 over bus 104. If the battery level is too low for reliable operation, then the CPR sequence continues as indicated. If the battery level is sufficient, then control passes to block 330 (FIG. 7b).

Block 330 prompts the operator to indicate whether or not the patient is unconscious. After generating this display, block 332 directs program execution to either block 338 or 334, depending upon whether or not the operator indicated that the patient was conscious the last time the question in block 330 was answered. If the patient was not conscious in the previous pass, then block 334 outputs a characteristic tone sequence. As indicated by block 336, this tone sequence continues until the operator responds by pushing either the YES or NO pushbutton switch. When the operator does respond, control passes to block 340. When the patient was conscious in the previous pass, then control passes directly from block 332 to block 338, where the program loops until the operator responds and then continues to block 340.

Block 340 determines whether the operator of the defibrillator has indicated that the patient is unconscious. If the patient is not unconscious, then block 342 outputs the display indicated in FIG. 3d, block 344 outputs a characteristic tone sequence, block 346 causes a four second delay, and program execution returns to block 330 to again ask whether the patient is unconscious. By such means, the defibrillator will be prepared to respond in an appropriate manner should a presently conscious patient later lose consciousness.

If the patient is unconscious, control passes to block 350 (FIG. 7c), and the message indicated in FIG. 3e is displayed. Block 352 then outputs a single tone through tone generator 108, and the program commences the collection of TTI (transthoracic impedance) and ECG data from the unconscious patient. As described previously, ADC 102 alternately supplies digital TTI and ECG samples to data processor 100, issuing interrupt signal RSTC whenever a sample is ready. Block 354 enables the RSTC interrupt, and the program then waits in block 356 for TTI data to be supplied. When an RSTC interrupt is received, program control is vectored to RSTC entry point 358, the data sample is input by block 360, and block 362 determines whether the sample is TTI or ECG data. If the sample is TTI data, then execution continues with block 364.

Block 364 analyzes successive TTI values to determine whether excessive motion is present in the patient. By way of example, block 364 could detect excessive motion by determining whether the last two TTI values exceed a threshold. If excessive motion is present, then block 366 generates the display indicated in FIG. 3f, block 368 causes production of a steady tone by tone generator 108, block 370 causes a one second delay, and block 372 determines whether the excessive motion has been present for 15 seconds. If it has not been present for 15 seconds, the program returns to block 350, and the data collection sequence is begun again. If excessive motion has been present for 15 or more seconds, then the program returns to block 316 (FIG. 7a), corresponding to the display in FIG. 3b.

The defibrillator of the present invention checks the patient for excessive motion because such motion could result in invalid ECG data, and because excessive motion could indicate that the patient should not be shocked. For example, excessive motion could indicate that the patient is conscious, that the patient is being moved, or that the patient is moving internally due, for example, to cardiac output.

If excessive motion is not present, then the defibrillator waits in block 374 for ECG data. When such data is ready, it is input by block 360, and block 362 directs program flow to block 376. Block 376 attenuates 60 Hz noise in the ECG data, and block 378 then tests the amplitude of the most recent ECG data point. If the amplitude is too large, block 380 decreases the gain of the analog preprocessor 140 by modifying gain select signal 156 (FIGS. 4a and 4b), and data collection is restarted at block 350. If the ECG amplitude is not too large, then block 382 provides a second level of filtering adapted to remove rumble below the ECG frequency range. If there is more data to be collected, block 384 then returns control to block 356 for acquisition of the next TTI and ECG data samples. When a sufficient number of ECG data samples have been collected and stored, control passes to block 386 in FIG. 7d.

Block 386 disables interrupt RSTC, thereby preventing ADC 102 from subsequently interrupting program flow. Block 388 then analyzes the ECG data points to determine the repetition rate (frequency) of the dominant complex in the ECG signal (e.g., the QRS complex). If the rate is less than 2.3 Hz or greater than 12 Hz, then block 390 directs program flow to block 392, where the shock flag for this pass is set to zero, indicating that the patient is not presently in a shockable condition. If the rate is within the shockable range, then block 394 checks to see whether the frequency variance of the ECG data exceeds a maximum limit. If the variance is too large, then the shock flag is set to zero in block 392. If the frequency variance is consistent with the application of defibrillation shock, then block 396 checks the average amplitude of the ECG signal. If the average amplitude is too low, then no conclusions can be reliably drawn from the data, and the shock flag is set to zero. If the amplitude is sufficient, block 398 determines whether R waves are present in the ECG signal. If R waves are present, then the patient should not be shocked, and the shock flag is set to zero in block 392. If R waves are not present, then block 400 performs a slope histogram analysis of the ECG data. In this analysis, the differences between adjacent ECG data points are determined, and the slopes (differences) falling within a series of ranges are counted. Block 402 then checks the relative frequency of low slope values. If such relative frequency is too high to be consistent with a shockable arrhythmia, then the shock flag is set to zero in block 392. If the relative frequencies of the lower histogram ranges are within shockable limits, then block 404 sets the shock flag for this pass to one, signifying that the patient's ECG signal indicates that a defibrillation shock is medically appropriate. It is to be understood that other known tests could be used, either singly or in combination, to determine whether a shockable ECG rhythm is present, and the invention herein is not limited to any particular method of making this determination.

The defibrillator makes two or three successive passes through the data acquisition and analysis steps just described. When the first pass is complete, blocks 406 and 408 direct program flow to block 350 (FIG. 7c) to begin the second pass. When the second pass is complete, block 410 checks the shock flag for the second pass. If the second shock flag is not equal to one, then control passes to block 438 (FIG. 7e) and a SHOCK NOT REQUIRED message is displayed to the operator. If both the first and second shock flags are equal to one, then control passes to block 416 (FIG. 7e), and a shock sequence is commenced. If the second shock flag is one, but the first shock flag is zero, then control returns to block 350, and a third pass is commenced. When the third pass is complete, block 406 directs control to block 414, and the third shock flag is tested to determine whether or not a shock should be administered.

If a shock is to be administered, then block 416 causes the data processor to drive line 200 high (FIG. 4b), enabling SHOCK pushbutton switch 56. Block 418 then causes generation of the display indicated in FIG. 3g, and block 420 causes production of a characteristic tone sequence. The program then executes a loop consisting of blocks 422 and 424 until the operator pushes the shock switch, or until 30 seconds have elapsed. If the shock switch is pushed, block 426 causes generation of the display indicated in FIG. 3h, block 428 causes output of a warning tone, block 430 sets variable CPR to 2, and block 432 then waits for processor controller 110 to issue READY and SHUT DOWN signals, as previously described. If the operator does not push the SHOCK switch within 30 seconds, block 434 causes line 200 to be pulled low, disabling the SHOCK switch. Block 436 then sets variable CPR equal to 4, and returns control to the CPR sequence commencing with block 316 (FIG. 7a).

Figure 7D:
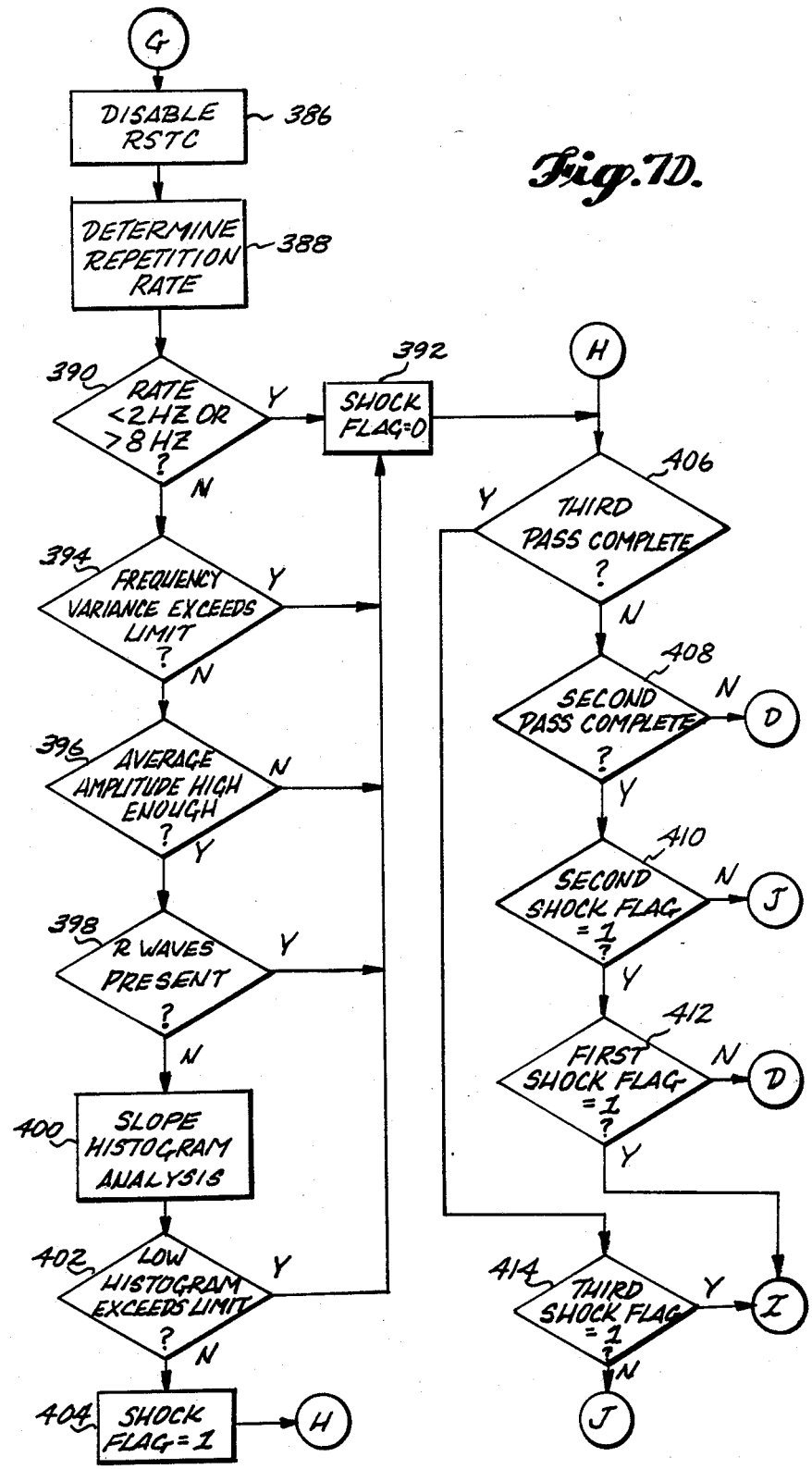
Figure 7E:
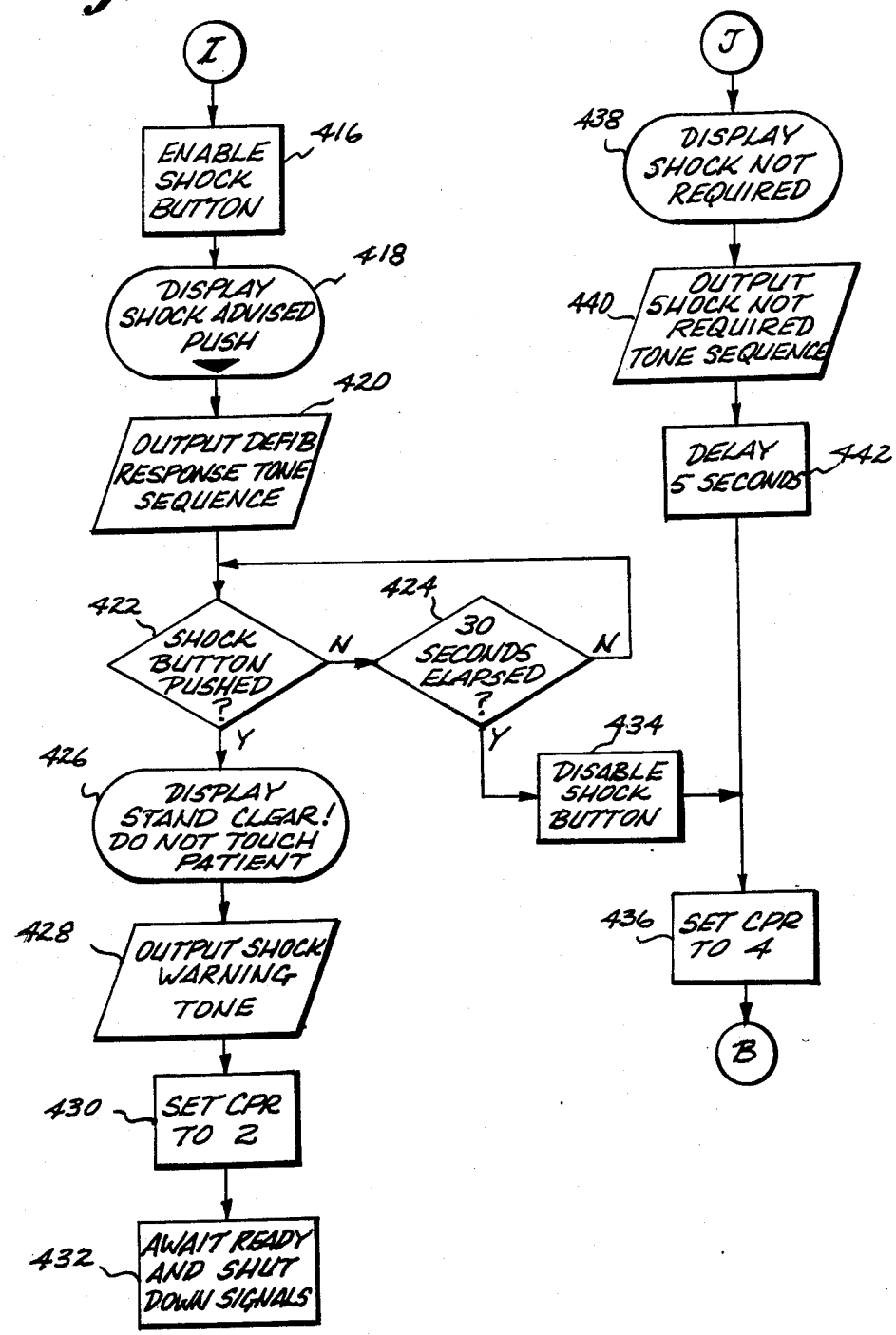

If the tests shown in FIG. 7d indicate that a shock is not to be applied, then control passes to block 438 where the indicated message is displayed. Block 440 then causes output of a characteristic tone sequence, and block 442 causes a 5 second delay. Block 436 then sets variable CPR to 4, and control returns to block 316.

The values of CPR set in blocks 430 or 436 will subsequently result in block 324 causing either 2 or 4 CPR sequences to be executed, depending upon whether or not a shock was administered to the patient.

While the preferred embodiments of the invention have been illustrated and described, it should be understood that variations will become apparent to those skilled in the art. Accordingly, the invention is not to be limited to the specific embodiments illustrated and described herein, but rather the true scope and spirit of the invention are to be determined by reference to the appended claims.

The embodiments of the invention in which an exclusive property or priviledge is claimed are defined as follows:

1. An interactive medical electronic device for obtaining information about a patient's condition directly from the patient and information pertinent to an analysis of the patient's condition indirectly through an operator of the device, and for producing a medically appropriate action in response thereto, said device comprising:
   (a) sensor means for obtaining direct information concerning the condition of the patient;
   (b) information processing means, comprising:
      (i) interactive communication means including means for obtaining indirect information pertinent to an analysis of the patient's condition from the operator, the means for obtaining indirect information comprising means for prompting the operator, and means for receiving the operator's response thereto; and
      (ii) control means for producing a control signal when said direct and indirect information indicates that the medically appropriate action should be taken; and
   (c) output means responsive to the control signal for producing said action upon the patient.

2. The device of claim 1, wherein the means for prompting the operator comprises means for communicating questions to the operator.

3. The device of claim 2, wherein the means for obtaining indirect information comprises means for communicating questions for which appropriate responses are either YES or NO.

4. The device of claim 3, wherein the means for receiving the operator's responses comprises first and second touch activated means, the first touch activated means corresponding to a YES response and the second touch activated means corresponding to a NO response.

5. The device of claim 1, wherein the interactive communication means includes means for communicating instructions to the operator.

6. The device of claim 1, wherein the information processing means comprises means for obtaining the assent of the operator before producing the control signal.

7. The device of claim 1, wherein the sensor means comprises means for detecting the electrical activity of the patient's heart.

8. The device of claim 7, wherein the output means comprises means for applying a defibrillation pulse to the patient.

9. The device of claim 8, wherein the means for determining indirect information comprises means for obtaining information indicating whether or not the patient is conscious.

10. The device of claim 9, wherein the means for obtaining indirect information comprises means for obtaining information indicating whether or not cardiopulmonary resuscitation has been performed on the patient.

11. The device of claim 8 or 10, wherein the interactive communication means includes means for communicating instructions to the operator.

12. The device of claim 11, wherein the interactive communication means includes means for instructing the operator to perform cardiopulmonary resuscitation on the patient.

13. The device of claim 8, wherein the information processing means comprises means for communicating a question regarding whether or not the patient is conscious, and means responsive to a response indicating that the patient is conscious for preventing production of the control signal and for continuing to communicate the said question regarding whether or not the patient is conscious, such that if the patient subsequently becomes unconscious the operator can respond appropriately.

14. The device of claim 8, wherein the information processing means comprises means for obtaining the assent of the operator before producing the control signal.

15. The defibrillator of claim 8, wherein the means for applying a defibrillation pulse includes energy storage means and means responsive to the control signal for charging the energy storage means up to a threshold level and then discharging the energy storage means through the patient without operator intervention.

16. The device of claim 1, wherein the sensor means comprises electrodes adapted to receive electric signals including an electrocardiogram signal from the patient, and electrocardiogram detection means connectable to the electrodes for receiving electrical signals from the electrodes and producing an ECG signal corresponding to the patient's electrocardiogram signal.

17. The device of claim 16, wherein the output means comprises means connectable to the electrodes for applying a defibrillation pulse to the patient through the electrodes.

18. The device of claim 17, wherein the sensor means comprises motion detection means connectable to the electrodes for producing a motion signal indicative of patient motion including patient motion not synchronized with the ECG signal, and wherein the control means comprises means for preventing the production of the control signal when excessive patient motion is detected.

19. The device of claim 18, wherein the control means comprises means for analyzing the ECG signal to detect the presence or absence of a shockable heart rhythm, means for analyzing the motion signal to detect the presence or absence of excessive motion, and means for producing the control signal only if shockable heart rhythm is present and if excessive motion is absent.

20. The device of claim 19, wherein the means for analyzing the ECG signal is adapted to analyzing the ECG signal during a predetermined length of time, and wherein the means for analyzing the motion signal includes means for terminating the analysis of the ECG signal when the presence of excessive motion is detected, whereby the control signal is not produced if excessive motion is detected.

21. A defibrillator for delivering a defibrillation shock to a patient, comprising:

information processing means for determining whether a defibrillation shock should be delivered and for providing a first control signal if said defibrillation shock should be delivered; and defibrillation means including energy storage means and charge control means responsive to the first control signal for charging the energy storage means and then discharging the energy storage means through the patient, the charge control means being operative to discharge the energy storage means through the patient when the charge on the energy storage means reaches a threshold level or when a predetermined time has elapsed after the first control signal, whichever occurs first.

22. The defibrillator of claim 21, wherein the defibrillation means comprises means for providing a second control signal whenever the energy storage means is discharged, and wherein the information processing means includes means for suspending its operations from the time that the first control signal is provided until the second control signal is provided.

23. The defibrillator of claim 22, wherein the first and second control signals are communicated between the information processing means and the defibrillation means through a single conductive line.

* * * * *